| United States Patent [19] | [11] Patent Number: 4,470,967 |
| Gough et al. | [45] Date of Patent: Sep. 11, 1984 |

[54] LECTIN-CONTAINING ANTI-VIRAL VACCINES FOR DOMESTIC ANIMALS AND METHOD OF PREPARATION

[75] Inventors: Patricia M. Gough; Kenneth B. Platt, both of Ames, Iowa

[73] Assignee: Iowa State University Research Foundation, Ames, Iowa

[21] Appl. No.: 432,820

[22] Filed: Oct. 5, 1982

[51] Int. Cl.³ .............................................. A61K 39/12
[52] U.S. Cl. ..................................................... 424/89
[58] Field of Search ...................... 424/89, 85, 86, 177; 260/112 R; 436/827, 828

[56] References Cited

U.S. PATENT DOCUMENTS

| 3,994,870 | 11/1976 | Neurath et al. | 260/112 R |
| 4,203,893 | 5/1980 | Pery et al. | 260/121 |
| 4,291,019 | 9/1981 | Lupton et al. | 424/89 |
| 4,335,105 | 6/1982 | Gough | 424/89 |
| 4,371,515 | 2/1983 | Chu | 436/544 |

OTHER PUBLICATIONS

Velicer et al., Journal of Virology, 1978, 27, 1, pp. 205–217.
Brown and Hunt, "Lectins", in International Review of Cytology, vol. 52, pp. 277–278, 292–297 (Academic Press, 1978).

*Primary Examiner*—Sidney Marantz
*Assistant Examiner*—Shawn P. Foley

[57] ABSTRACT

Anti-viral vaccines for domestic animals are prepared from glycoprotein envelope whole virus or antigenic glycoprotein obtained therefrom by complexing the glycoprotein antigenic agent with a lectin, which is preferably a mitogenic lectin. The recovery of the immunizing agent from an aqueous solution or suspension is facilitated since the lectin-glycoprotein complex is readily recoverable. The mitogenic lectin administered in the vaccine with the glycoprotein antigen can enhance the anamnestic response, in effect, acting as an adjuvant.

17 Claims, No Drawings

LECTIN-CONTAINING ANTI-VIRAL VACCINES FOR DOMESTIC ANIMALS AND METHOD OF PREPARATION

GRANT REFERENCE

The invention described herein was made in the course of work under grant from the United States Department of Agriculture, No. 58-519B-1-0999.

FIELD AND OBJECTIVES OF INVENTION

The field of this invention is anti-viral vaccines prepared either from aqueous suspensions of whole virus, or from aqueous solutions of subunit antigenic viral protein. More particularly, the invention relates to anti-viral vaccines in which the immunizing agent has antigenic glycoprotein in the viral envelope or consists of separated glycoprotein. The method is highly advantageous for preparing vaccines from solublized glycoprotein for administration to domestic animals.

The objectives of this invention involve the recovery of the viral antigen agent in purified form, and its incorporation in a parenteral vaccine of enhanced immunogenicity. To provide anti-viral vaccines of improved effectiveness, it is desirable to recover the intact virus, or solubilized antigenic protein components thereof in a relatively pure concentrated form. In the preparation of vaccines from bacterial cells, the cells can be readily separated from the culture media suspensions by centrifigation, and after separation, they can be washed to remove soluble residues. Viruses and subunit viral proteins are much more difficult to prepare as purified concentrates.

Viruses for vaccine use are produced in cell-containing media, the host cells or adapted tissue cells serving as the means for the propagation of the virus. The cells can be lysed to liberate the virus, but it is difficult to efficiently separate the viral particles from other residues of the media. Such separation may be even more difficult where the viral protein is solubilized, such as by the action of a nonionic detergent, the antigenic proteins being in solution together with other soluble substances.

There has been a recognized need for better methods of recovering and concentrating viruses and viral antigenic proteins for use in preparing vaccines.

A somewhat related problem is that of improving the immunogenic response to parenterally administered anti-viral vaccines. The effectiveness of such response depends on the concentration and the amount of the specific antigenic agent administered. The antigenic protein of greatest effectiveness may be only one or a small number of the proteins of the virus. Therefore, ideally, the proteins of the virus are solubilized and fractionated to obtain the specific antigenic proteins for the vaccine.

Anti-viral vaccines for domestic animals also utilize additives which are non-immunizing in themselves, but which enhance the immunogenic response. Such additives are usually referred to as adjuvants. However, the known adjuvants for this purpose vary in effectiveness with different viral antigens, or have undesirable side effects such as causing abscesses, or leaving unwanted residues in meat-producing animals.

SUMMARY OF INVENTION

It is known that certain lectins, such as lentil bean lectin or jack bean lectin (concanavalin A), selectively bind to viral glycoproteins. It is further known that enveloped virus usually contain one or more glycoproteins in the envelope surfaces of the virus. It is also known that certain lectins that are classified as mitrogenic lectins have the ability to bind to erythrocytes and to lymphocytes. The present invention utilizes this prior art knowledge to provide a novel process for the preparation of anti-viral vaccines, which vaccines in their preferred form contain a mitogenic lectin in an adjuvant effective amount.

In preferred embodiments, a mitogenic lectin, such as lentil bean lectin, is reacted with an aqueous suspension or solution of the glycoprotein antigenic substance to produce a glycoprotein-lectin complex which can be readily recovered from the solution, such as by ordinary centrifugation, and which after recovery is incorporated in the dose form of the vaccine without removal of the lectin. Preferably, a sufficient amount of the lectin is employed to form the complex so that excess lymphocyte-binding sites are provided. These binding sites are available in the vaccine for interaction with the T and/or B lymphocytes. It is believed that this action will enhance the immunogenic response of the animal to the vaccine.

The method of this invention and the vaccines produced thereby can be applied with particular advantage to the preparation of subunit viral glycoprotein vaccines. This invention provides an efficient way of preparing such vaccines on a commercial basis. Such vaccines can be used in conjunction with programs for eradication of viral diseases. The immunity produced by a subunit vaccine can be distinguished from the immunity following natural infection because a larger compliment of antibody specificities will be present after natural infection and recovery.

DETAILED DESCRIPTION

The starting materials for use in practicing the present invention are animal-disease producing viruses which are propagated by standard cell culture procedures. The class of disease-producing animal virus includes the viruses having envelopes containing one or more glycoproteins. For example, the virus may be transmissable gastroenteritis (TGE) virus, pseudorabies (PR) virus, both of which infect swine, or infectious bovine rhinotracheitis (IBR) virus, which infects cattle. Procedures for propagation, respectively of TGE and IBR virus are described in U.S. Pat. Nos. 4,335,105 and 4,291,015. A literature reference describing a procedure for propagation of PR virus is "The evaluation of an experimental porcine herpesvirus I (Aujexsky's disease virus) subunit vaccine in mice", D. L. Rock and D. E. Reed, Vet. Micro. 5(1980) p. 291-299.

More generally, the method of this invention can be used to prepare vaccines for immunizing against a wide variety of viral diseases of domestic animals. The following list is illustrative, of diseases and virus classifications to which the present invention is applicable.

| Disease Classification | Virus Classification |
| --- | --- |
| 1. Porcine diseases | |
| African swine fever | Iridovirus |
| Pseudorabies | Herpesvirus |
| Rabies | Rhabdovirus |
| Transmissible gastroenteritis | Coronavirus |
| Vomiting and wasting disease | Coronavirus |
| 2. Bovine diseases | |

| Disease Classification | Virus Classification |
| --- | --- |
| Bovine herpes mammillitis | Herpesvirus |
| Bovine leukosis | Oncovirus (Retroviridae) |
| Infectious bovine rhinotracheitis | Herpesvirus |
| Malignant catarrhal fever | Herpesvirus |
| Parainfluenza - 3 | Paramyxovirus |
| Pseudorabies | Herpesvirus |
| Rabies | Rhabdovirus |
| Rinderpest | Paramyxovirus |
| Slow herpesvirus (DN 599) | Herpesvirus |
| 3. Ovine and caprine diseases | |
| Border disease | Togaviridae |
| Caprine arthritis-encephalitis | Retroviridae |
| Louping ill | Togaviridae |
| 4. Equine diseases | |
| Equine infectious anemia | Retroviridae |
| Equine influenza | Orthomyxovirus |
| Equine viral arteritis | Togaviridae |
| 5. Canine diseases | |
| Canine coronavirus infection | Coronavirus |
| Canine herpesvirus infection | Herpesvirus |
| 6. Feline diseases | |
| Feline rhinotracheitis | Herpesvirus |

After the envelope glycoprotein virus for preparing the vaccine has been propagated by cell culture, the cells are ruptured (lysed), such as by sonication, to liberate the viral particles into the aqueous medium. The residue solids of the cell mass can be separated by centifigation, leaving the viral particles in the aqueous medium, which will also contain other soluble components such as proteins. If the vaccine is to be prepared from whole virus, the virus can be inactivated by the addition of a suitable inactivating agent, such as formalin or merthiolate. Alternatively, if a subunit viral vaccine is to be prepared from the glycoproteins of the viral envelope, the virus can be dissolved by the addition of a solubilizing agent, such as a nonionic detergent, or a proteolytic enzyme. With virus which cause modification of the cell membranes during the viral replication process, the cell membranes may serve as a source of viral envelope glycoproteins which can be extracted by non-ionic detergents. By whatever means produced, the viral immunizing agent is recovered from the aqueous suspension or solution by complexing with a reactive lectin.

In general, the lectins which may be used are those which bind to glycoproteins. The selected lectin should be capable of complexing with the glycoprotein of the viral envelope or with the separated glycoproteins in the solution of the particular virus being prepared as a vaccine. Such lectins include lentil bean lectin, jack bean lectin (concanavalin A) and other similar lectins, some of which are characterized by their ability to agglutinate erythrocytes. Such lectins also contain multiple binding sites which are reactive with T and/or B lymphocytes. The preferred class of such lectins are the mitogenic lectins, like lentil bean and jack bean lectin, which promote mitogenesis of lymphocytes, that is, T cells, or B cells, or both. For other suitable lectins and a discussion of lectins, their glycoprotein reactivities and mitogenic properties, see Brown and Hunt, "Lectin", in International Review of Cytology, Vol. 72, pages 277–366 (Academic Press, 1978).

For use in the present invention, the complex forming, mitogenic lectin may be in water-soluble form, or it may be immobilized on a particular support. Unbound water-soluble lectins are preferred. However, bound forms of the lectins can be used and are commercially available, such as Con A Sepharose, providing immobilized concanavalin A lectin, and/or Lentil Lectin-Sepharose 4B, providing immobilized reactive lentil lectin, as supplied commercially by Pharmacia Fine Chemicals, a division of Pharmacia, Inc., Piscataway, N.J.

The glycoprotein immunizing agent in the aqueous solution or suspension is contacted with the lectin by dissolving it in the solution, and/or by adding the immobilized lectin in a particulate form to the aqueous solution or suspension, or by passing the aqueous solution or suspension through a column packed with granules of the immobilized lectin. The preferred procedure is to add the lectin directly to the aqueous suspension or solution. Whatever the procedure, a sufficient amount of the lectin reagent is employed to complex with the antigenic glycoprotein, and to form a readily separable complex therefrom. Where the lectin is added directly to the solution or suspension, the complex will form a precipitate, which will separate on standing, or which can be easily separated from the residual solution by centrifugation. Where the contacting is carried out in a column procedure, the glycoprotein antigen will be held up by selective adsorption on the bound lectin, while the residual solution will pass through and out of the column. The column material containing the adsorbed glycoprotein can then be removed from the column, after washing, if desired, and can be used for preparation of the vaccine. In the preferred procedure, the separated precipitate will be used to prepare the vaccine in the same manner. Where the glycoproteins of the viral envelope are first solubilized, as is particularly advantageous, the lectin is preferably added in water-soluble form, and is reacted with the dissolved glycoprotein components to form the recoverable precipitate, which is used to prepare the vaccine.

A sufficient amount of the lectin complexing agents should be employed to form a readily separable complex with the immunizing agent. The amount required will depend on the amount of glycoprotein present, the number of respective binding sites on the lectin and on the glycoprotein, and whether the lectin is in immobilized form, or whether both the lectin and the glycoprotein are in solution. In general, from 0.01 to 0.1 milligrams (mg) of the lectin may be employed per milligram of the glycoprotein. For example, amounts of lectin ranging from about 50 to 200 micrograms per milligram of glycoprotein can be used. Excess lectin may be present. Further, in order to facilitate binding of the complexed lectin with the lymphocytes, the lectin in complexed form should still have unoccupied binding sites available for lymphocyte binding.

After recovery, the complexed immunizing agent is prepared in vaccine dose form for administration to the domestic animal. Where the complexed immunizing agent is used without a standard adjuvant, it may be prepared in dose form by suspension in buffered saline, such as a sterile phosphate-buffered saline solution. Alternatively or additionally, however, standard adjuvant compositions can be combined with the immunizing agent to further enhance the immunogenic response. For example, an aluminum hydroxide adjuvant can be employed, or an oil-type adjuvant, such as Fruend's Incomplete Adjuvant. In preferred embodiments, however, where the lectin of the complex is a lectin which is mitogenic for lymphocytes and where the complex lectin provides available sites for binding with the lymphoctye, an additional standard adjuvant of the kind previously used in vaccines for domestic animals need not be employed.

The dose form of the vaccine should be an injectable liquid suspension. The mode of injection may be subcutaneous or intramuscular, or other parenteral injection site. The dose form should be in convenience size volumes for injection; such as 0.5 or 1.0 milliliter doses. The amount of the immunizing agent present on the basis of the glycoprotein present will vary with the particular vaccine, and the potency of the immunizing agent. In general, however, a vaccine dose form to be given as one dose per animal may contain from about 10 to 1000 micrograms of immunizing glycoprotein.

The method of this invention and the vaccines which can be produced thereby are further illustrated by the following examples.

EXAMPLE I

A. Preparation Lectin-PRV Vaccine

1. Pseudorabies virus are propagated by cultivation of the virus in a pig kidney cell line. The virus infected cells are harvested when 100% of the cell monolayer shows cytopathic effect.

2. The cells are washed and then extracted with a 1% solution of Triton-X-100 prepared in Tris/Tricine buffer 0.025M pH 8.6. The detergent solution is added at the rate of 1 ml per 1 ml cell volume. Cell volume is determined by pelletting the cell suspension at 800×g for 20 minutes. The cells are then resuspended and sonically disrupted. The disrupted suspension is then gently agitated for a minimum of 1 hour at 4° C. The suspension is then clarified by low speed centrifugation followed by centrifugation at 100,000×g for 90 minutes. The clear middle layer is harvested and used as crude antigen. The upper cloudy layer is first treated with freon to remove lipids and also used as crude antigen. The protein concentration of this preparation usually ranges between 6 and 7 mg/ml. The two layers are combined.

3. Glycosylated viral antigens are extracted from crude antigen with lentil bean lectin. The lectin is commercially supplied conjugated to agarose beads. Equal volumes of agarose-lectin and the combined crude antigen are mixed together and permitted to react overnight at 4° C. The preparation is then washed to remove non-adsorbed antigen. This preparation is then mixed 1:1 with Freund's incomplete adjuvant and used as vaccine.

B. Pig Immunization Studies

Three expirements were conducted.

In Experiment I, 3 pigs were inoculated with $2\frac{1}{4}$ ml of vaccine containing approximately 0.5 mg of protein extracted from the cytoplasmic membrane of virus infected cells. The injections were at multiple subcutaneous sites in equally apportioned volumes. Twenty-one days layer the pigs received a second inoculation of the vaccine. Three weeks after the second vaccine dose the 3 vaccinated and 4 control litter mates were challenged with virulent pseudorabies virus. The effectiveness of the vaccine was measured by the humoral antibody response it elicited, by its ability to reduce the amount of virus excreted, by its ability to reduce death losses and by its ability to minimize loss in rate of weight gain.

Experiment II was conducted in the same manner except that 4 vaccinates and 5 controls were used. The results of Experiment I are summarized below in Tables A1 and A2, and the results for Experiment II are summarized in Tables B1 and B2.

Experiment III was conducted to determine if two single inoculations of 1 ml volume given at a 21 days interval, and containing approximately 0.15 mg of protein extracted from cytoplasmic membrane infected cells would protect pigs from virulent virus. Two pigs received the vaccine and three pigs served as controls. All control pigs died after being challenged with $10^8$ PFU of virus via the nasal route. Conversely the two vaccinated pigs survived.

TABLE A1

Antibody Response of Vaccinated Pigs (Experiment I).

| Days Post Inoculation | Titer[a] Range | Titer Geo. $\bar{X}$[b] |
|---|---|---|
| 21 (2nd Inoculation) | 2-4 | 2.5 |
| 35 | 16-64 | 32.0 |
| 42 (Day of virus challenge) | 16-64 | 32.0 |
| 52 | 512-512 | 512.0 |
| 59 | 256-512 | 405.0 |

[a] n = 3
[b] Titer determined by the serum neutralization/plaque reduction test, and shown as geometric mean (Geo. $\bar{X}$)

TABLE A2

Rate of Weight Gain of Vaccinated and Control Pigs Before and After Virus Challenge (Experiment I).

| | Rate of Gain (lbs/day) | |
|---|---|---|
| Time Period[a] | Vaccinates[b] | Controls[c] |
| Day −7 to 0 | +1.76 | +1.94 |
| Day 0 to 4 | −1.25 | −1.48 |
| Day 4 to 17 | +1.62 | All Controls dead w/i 6 days |

[a] Day 0 = day on which all pigs were challenged with virulent virus.
[b] n = 3
[c] n = 4

TABLE B1

Antibody Response of Vaccinated Pigs (Experiment II).

| Days Post Inoculation | Titer[a] Range | Titer[b] Geo. $\bar{X}$ |
|---|---|---|
| 21 (2nd inoculation) | 4-16 | 5.7 |
| 35 | 32-128 | 64.0 |
| 42 (day of virus challenge) | 16-64 | 45.3 |
| 52 | 512-4096 | 1024.0 |
| 59 | 512-4096 | 1217.7 |

[a] n = 4
[b] Titer determined by the serum neutralization/plaque reduction test, and shown as geometric mean (Geo. $\bar{X}$).

TABLE B2

Rate of Weight Gain of Vaccinated and Control Pigs Before and After Virus Challenge (Experiment II).

| | Rate of Gain (lbs/day) | |
|---|---|---|
| Time period[a] | Vaccinates[b] | Controls[c] |
| Day −7 to 0 | +1.29 | +1.28 |
| Day 0 to 4 | −.93 | −1.50 |
| Day 4 to 17 | +1.42 | All controls dead |

[a] Day 0 = day on which all pigs were challenged with virulent virus.
[b] n = 4
[c] n = 5

EXAMPLE II

A transmissable gastroenteritis (TGE) virus subunit vaccine is prepared as follows:

A. Culturing of Virus:

1. The TGEV is produced from the virulent Illinois isolant of TGEV, which is replicated in small intestines of baby SPF pigs (infected at 48 hrs. of age, virus generally harvested 48 hrs. post-infection). A 20% suspension of the ground jejunum of the infected pigs is made in minimum essential medium (Eagle's) to which 5% lactalbumin hydrolysate, 2% fetal porcine serum and antibiotics have been added. 3 ml. of the suspension are used to inoculate 150 cm² swine testes cells for in vitro propagation of virus. The cells are 6-day-old (post-passage) monolayers when infected and harvest of virus is done at 3 days post-inoculation. Higher titers of virus are obtained with older cells (6 to 8 days) than with younger (3 to 5 days) cells. This is especially important with strains of TGE virus (such as Illinois) which are not well-adapted to in vitro conditions. Virus is collected after two freeze-thaw cycles of cells-medium.

B. Release of Subunit from Virion:
1. Crude virus suspension is clarified by centrifugation at 5000×g for 30 minutes.
2. Proteins are precipitated with 7% polyethylene glycol 6000–2.3% sodium chloride at 40° C. for 1 hour and the precipitate is collected following centrifugation at 5000×g for 30 minutes. The precipitate is suspended in trissaline buffer to 1/20th the original volume.
3. Bromelain is added to the virus solution at a concentration of 1 mg enzyme/ml virus. Tne mixture is held at 37° for 1 hour for proteolysis to occur after which the reaction is stopped with 1 mM p-chloromercuribenzoate.

C. Preparation of Lentil Bean Lectin:
1. Lentil beans (20 gm) are homogenized in 80 ml of phosphate-buffered saline in a blender.
2. The mixture is centrifuged at 5000×g for 30 minutes.
3. The lectin is the supernatant is adsorbed on 3-ml column of Affi-Gel Ovalbumin. The column is washed with phosphate-buffered saline to remove unadsorbed substances.
4. The lectin is eluted with 0.5M alpha-methyl mannoside.

D. Precipitation of Subunit With Lectin:
1. Equal volumes of Lectin and subunit are mixed with stirring and the mixture is let stand at 4° C. overnight.
2. The precipitate complex is collected by centrifugation at 5000×g for 20 minutes.

E. Preparation of Vaccine:
The precipitate is suspended in phosphate-buffered saline to give a solution containing 1 mg of protein/ml. One dose of the vaccine consists of 1 ml.
The vaccine is administered intramuscularly (IM).

The vaccine prepared as described above was tested for efficacy as follows:

Test for Lactogenic Immunity

Two first litter gilts were immunized (IM) with 1 ml of the suspension of TGEV subunit-lectin 6 weeks prior to farrowing. A second dose of vaccine was given 4 weeks later. An unimmunized gilt served as a control in the test. Baby pigs nursing on the gilts were challenged with 100 PID50 virulent TGEV Illinois strain at 3 days of age and were observed for clinical signs of TGE. Attempts were made to isolate TGEV from the baby pigs and TGEV was identified by straining of intestinal sections with specific fluorescent antibody.

Mild and intermittent diarrhea was observed in the pigs on one vaccinated gilt but serious disease did not occur and there were no deaths. No clinical disease was evident in the pigs on the other immunized gilt. All control pigs became ill and mortality was 80% (4 of 5 animals). TGEV was isolated from control but not from experimental pigs.

Test for Local Immunity in Small Intestine

Fifteen yound weaned pigs (40 lbs. at start of the experiment) were immunized in the same manner as the gilts. Two doses of vaccine were given 4 weeks apart. Six additional pigs served as controls. Four weeks later the animals were challenged with $10^5$ PID50 virulent TGE virus, Illinois strain, and were observed for signs of clinical TGE. Three experimental and all control animals became ill. Attempts made to reisolate TGEV were successful for all sick pigs. Sero conversion of animals to TGEV was determined.

We claim:
1. A veterinary vaccine in parenterally injectable dose form, comprising an effective immunizing dose amount of viral antigen immunizing agent selected from the class consisting of (i) whole viruses having envelopes containing at least one glycoprotein or (ii) the separated viral envelope glycoprotein obtained from such viruses, and a mitogenic lectin complexed with the glycoprotein of said immunizing agent, said complexed lectin providing binding sites available for lymphocytes, and said vaccine containing at least from 0.01 to 0.1 milligrams (mg) of said mitogenic lectin per milligram (mg) of glycoprotein.
2. The vaccine of claim 1 in which said immunizing agent comprises transmissible gastroenteritis (TGE) virus or separated glycoprotein obtained therefrom.
3. The vaccine of claim 2 in which said immunizing agent comprises separated TGE envelope glycoprotein.
4. The vaccine of claim 1 in which said immunizing agent comprises pseudorabies (PR) virus or glycoprotein obtained therefrom.
5. The vaccine of claim 4 in which said immunizing agent comprises separated pseudorabies °PR1 envelope glycoprotein.
6. The vaccines of claims 1 to 5 in which said lectin is lentil bean lectin.
7. The method of preparing and administering a veterinary vaccine, comprising:
   (a) preparing an aqueous solution or suspension of a viral antigen immunizing agent selected from the class consisting of (i) whole viruses having envelopes containing at least one glycoprotein or (ii) the separated viral envelope glycoprotein obtained from such viruses;
   (b) contacting said immunizing agent in said aqueous solution or suspension with a lectin reagent capable of complexing with the glycoprotein of said immunizing agent, said lectin reagent being a mitogenic lectin and a sufficient amount of said lectin reagent being employed to form a readily separable complex from said immunizing agent;
   (c) recovering the thus-formed lectin-glycoprotein complex of the immunizing agent;
   (d) preparing a parenterally injectable vaccine from said immunizing agent without separating the lectin therefrom, the lectin in said complex having binding sites available for lymphocytes; and
   (e) administering an effective immunizing dose amount of said vaccine by parenteral injection to an animal capable of being immunized by said immunizing agent.

8. The method of claim 7 in which said lectin is in water-soluble form when complexed with said immunizing agent.

9. The method of claim 7 in which said lectin when complexed with said immunizing agent is immobilized on a particulate support material.

10. The method of claims 7, 8, or 9 in which said lectin is lentil bean lectin.

11. The method of claims 7, 8, or 9 in which said immunizing agent comprises transmissible gastroenteritis virus or separated glycoprotein obtained therefrom.

12. The method of claims 7, 8, or 9 in which said immunizing agent comprises pseudorabies (PR) virus or separated glycoprotein obtained therefrom.

13. The method of claim 7 in which said immunizing agent is separated viral envelope glycoprotein, and both said glycoprotein and said lectin are dissolved in said aqueous solution for said complexing reaction.

14. The method of claim 13 in which said glycoprotein is obtained from transmissible gastroenteritis (TGE) virus, and said lectin is lentil bean lectin.

15. The method of claim 13 in which said glycoprotein is obtained from pseudorabies (PR) virus, and said lectin is lentil bean lectin.

16. A veterinary vaccine in parenterally injectable dose form, comprising an effective immunizing dose amount of viral antigen immunizing agent consisting of viral envelope glycoprotein separated from a virus having an envelope containing at least one glycoprotein, and a mitogenic lectin complexed with said immunizing agent, said complexed lectin providing binding sites available for lymphocytes, and said vaccine containing at least from 0.01 to 0.1 milligrams (mg) of said mitogenic lectin per milligram (mg) of glycoprotein.

17. The method of preparing and administering a veterinary vaccine comprising:
   (a) preparing an aqueous solution of a viral antigen immunizing agent consisting of separated viral envelope glycoprotein obtained from a virus having an envelope containing at least one glycoprotein;
   (b) contacting said immunizing agent in said aqueous solution with a lectin reagent capable of complexing with the glycoprotein of said immunizing agent, said lectin reagent being a mitogenic lectin and a sufficient amount of said lectin reagent being employed to form a readily separable complex from said immunizing agent;
   (c) recovering the thus-formed lectin-glycoprotein complex;
   (d) preparing a parenterally injectable vaccine from said immunizing agent without separating the lectin therefrom the lectin in said complex having binding sites available for lymphocytes; and
   (e) administering an effective immunizing dose amount of said vaccine by parenteral injecting to an animal capable of being immunized by said immunizing agent.

* * * * *